US005409905A

United States Patent [19]

Eby, III

[11] Patent Number: 5,409,905
[45] Date of Patent: * Apr. 25, 1995

[54] CURE FOR COMMOND COLD

[76] Inventor: George A. Eby, III, 2109 Paramount Ave., Austin, Tex. 78704

[*] Notice: The portion of the term of this patent subsequent to Mar. 10, 2009 has been disclaimed.

[21] Appl. No.: 215,008

[22] Filed: Mar. 21, 1994

Related U.S. Application Data

[63] Continuation of Ser. No. 42,473, Apr. 2, 1993, abandoned, which is a continuation-in-part of Ser. No. 799,607, Nov. 27, 1991, abandoned, which is a continuation-in-part of Ser. No. 633,043, Dec. 24, 1990, Pat. No. 5,095,035, which is a continuation-in-part of Ser. No. 182,983, Apr. 18, 1988, Pat. No. 5,002,970, and a continuation-in-part of Ser. No. 102,750, Sep. 24, 1987, Pat. No. 4,956,385, which is a continuation of Ser. No. 667,097, Nov. 1, 1984, abandoned, which is a continuation-in-part of Ser. No. 378,479, May 14, 1982, Pat. No. 4,503,070, which is a continuation-in-part of Ser. No. 288,750, Jul. 31, 1981, abandoned, which is a continuation-in-part of Ser. No. 222,620, Jan. 5, 1981, abandoned.

[51] Int. Cl.⁶ .......................... A61K 9/14; A61K 9/20; A61K 31/315; A61K 33/30
[52] U.S. Cl. ........................ 514/23; 424/435; 424/440; 424/464; 424/468; 424/489; 514/494; 514/777; 514/849; 514/888; 514/889; 514/948; 514/964; 514/965; 514/974
[58] Field of Search ................ 514/23, 494, 777, 849, 514/888, 889, 948, 964, 965, 974; 424/435, 440, 464, 468, 489

[56] References Cited

U.S. PATENT DOCUMENTS

| Re. 33,465 | 11/1990 | Eby | 514/494 |
|---|---|---|---|
| 3,888,976 | 6/1975 | Mlkyvy | 424/49 |
| 4,059,686 | 11/1977 | Tanaka et al. | 426/549 |
| 4,261,982 | 4/1981 | Luedders et al. | 536/9 |
| 4,382,924 | 5/1988 | Berling et al. | 426/548 |
| 4,469,684 | 9/1984 | Huggins et al. | 514/859 |
| 4,503,070 | 3/1985 | Eby | 514/494 |
| 4,684,528 | 8/1987 | Godfrey | 424/49 |

(List continued on next page.)

FOREIGN PATENT DOCUMENTS 3001575 7/1981 Germany.
3629107 3/1988 Germany.

OTHER PUBLICATIONS

Farr et al., Antimicrobial Agents & Chemotherapy, 1987; 31:1183–1187.

(List continued on next page.)

Primary Examiner—Ronald W. Griffin

[57] ABSTRACT

Present invention is a non-toxic, flavor stable, pleasant tasting composition releasing $Zn^{2+}$ from compositions containing a highly ionizable zinc compound other than zinc gluconate that reduces the duration of common colds in humans. The composition is used in the oral cavity of a human suffering from a common cold. The composition comprises highly ionizable zinc compounds and a pharmaceutically acceptable carrier such as fructose, dextrose or sucrose with various additions. Compositions are unique in that they are non-toxic, pleasant tasting and do not have an offensive aftertaste, yet deliver zinc ions into oral tissues which may be used to treat common colds, reduce the duration of common colds or cure common colds in humans in need of such treatment. Compositions are non-toxic, thermally, chemically and flavor stable. The compositions may be prepared in the form of compressed tablets, lozenges, powders, liquids or chewing gums. Present compositions deliver strongly antirhinoviral and interferon inducing $Zn^{2+}$ions to the oral mucosa of a human. In vitro, $Zn^{2+}$ is as antirhinoviral and as protective of cell monolayers as interferon and is also a potent interferon inducer. Said pleasant tasting composition is an improvement upon a slow-release candy composition comprising a hard candy base, highly ionizable zinc compounds and an amino acid; and said composition is an improvement upon a medicinal composition for release of zinc ion consisting essentially of a suitable pharmaceutical carrier, highly ionizable zinc compounds and anethole.

23 Claims, No Drawings

U.S. PATENT DOCUMENTS

| | | | |
|---|---|---|---|
| 4,721,716 | 1/1988 | Neesby | 514/557 |
| 4,956,385 | 9/1990 | Eby | 514/494 |
| 5,002,970 | 3/1991 | Eby | 514/494 |
| 5,059,416 | 10/1991 | Cherukuri et al. | 424/48 |
| 5,095,035 | 3/1992 | Eby | 514/494 |
| 5,286,748 | 2/1994 | Eby | 514/494 |

OTHER PUBLICATIONS

Douglas et al., Antimicrobial Agents & Chemotherpay, 1987; 31:1263–1265.
CFR Title 21 §170.50, Glycine in Food for Human Consumption.
Godfrey et al., The Journal of International Medical Research, 1992; 20:234–246.
Cecchin. Medical World News, 1993 Mar. pp. 30–42.
Eberlein. Redbook Magazine. Dec. 1993:53–56.
Gwaltney. Bottom Line Personal. Mar. 1988:11–12.
B. D. Korant et al., Nature. 1974; 248:588–590.
Korant & Butterworth. Journal of Virology, 1971; 18:298–306.
Butterworth et al., Archives of Virology 1976; 51:169–189.
Korant. Chemical Abstracts 85:76 Abst. No. 814y.
Korant, "Role of Cellular and Viral Protenses in the Processing of Picornavirus Proteins", In: The Molecular Biology of Picornaviruses. 1979:149–173, Perez Bercoff Ed. Plenum Press.
Korant "Inhibition of Viral Proteins Geavage" In: Design of Inhibitors of Viral Functions. Igauri ed. Academic Press.
Merluzzi et al. Research Communications on Chemical Pathology and Pharmacology. 1989; 66:425–440.
Geist et al. Antimicrobial Agents & Chemotherapy. 1987; 31:622–624.
Salas & Kirchner. Clinical Immunology and Immunopathology. 1987; 45:139–142.
Eby et al. Antimicrobial Agents & Chemotherapy. 1984; 25:20–24.
Al–Nakib. Journal of Antimicrobial Chemotherapy. 1987; 20:893–901.
Smith et al. Antimicrobial Agents & Chemotherapy 1989; 33:646–648.
Berthon, May & Williams, Journal of the Chemical Society, Dalton 1978; 1433–1438.
Letter from R. J. E. Williams to R. M. Douglas. Aug. 27, 1987.
Figure from Guy Berthow—Zinc Species in Zine Gluconate–Glycine.
CFR Title 21 Paragraph 170.50 Glycine in Food for Human Consumption.
Pasternak BioAssays 1987; 6:14.
Pasternak, Bioscience Reports. 1987; 7:81–91.
Bashford, et al. J. Bio Chem. 1986; 261:9300.
Bashford, et al., J. Immunol. 1988; 141:3965.
Bashford, et al. J. Membrane Biol. 1988; 103:79.
Chvadil, Med. Clinic North America 1976; 60:799.
Osol A, Remington's Pharmaceutical Sciences, 16 Edition 1980:720.
Eby, "The Zinc and Common Cold Story" In: Guy Berthon Ed. Handbook on Metal Ligand Interaction of Biological Fluids, Marcel Dekker Inc. 1994.
Eby, G. A., Draft Copy of Handbook for Curing the Common Cold (The Zinc Lozenge Story) 1993.
Briggs et al., Carbohydrate Research. 1981; 97:181.

CURE FOR COMMOND COLD

This application is a continuation of application Ser. No. 08/042,473, filed on Apr. 2, 1993, now abandoned, which is a continuation-in-part of U.S. Ser. No. 07/799,607, filed Nov. 27, 1991, abandoned, which is a continuation-in-part of U.S. Ser. No. 07/633,043, filed Dec. 24, 1990, now U.S. Pat. No. 5,095,035, which is a continuation-in-part application of U.S. Ser. No. 07/182,983, filed Apr. 18, 1988, now U.S. Pat. No. 5,002,970, and a continuation-in-part of application U.S. Ser. No. 07/102,750, filed Sep. 24, 1987, now U.S. Pat. No. 4,956,385, which is a continuation of application Ser. No. 06/667,097, filed Nov. 1, 1984, now abandoned, which is a continuation-in-part application of Ser. No. 06/378,479, filed May 14, 1982, now U.S. Pat. No. 4,503,070, issued Mar. 5, 1985, reissued on Nov. 27, 1990, as RE 33,465, which is a continuation-in-part application of U.S. Ser. No. 06/288,750, filed Jul. 31, 1981, now abandoned, which is a continuation-in-part application of U.S. Ser. No. 06/222,620, filed Jan. 5, 1981, now abandoned.

FIELD OF INVENTION

This invention relates to medicinal or nutritional compositions containing non-toxic, highly ionizable zinc compounds for oral absorption by humans. More particularly, this invention relates to non-toxic, chemically, thermally and flavor stable compositions containing non-toxic, highly ionizable zinc compounds and pharmaceutically acceptable carriers, preferably those that are sweet such as fructose, sucrose and the like that reduce the duration of common colds. Other necessary ingredients are described as extra sweeteners, flavors, stabilizers and lubricants, when making compressed tablets; gum bases, sugars and flavors, when making chewing gum; water and sugars when making syrups and so forth. Such compositions when applied to oral and oropharyngeal membranes of a human are palatable, non-toxic and without undesirable taste or aftertaste yet allow absorption of hydrated zinc ions ($Zn^{2+}$) into oral and oropharyngeal tissues. Said absorption of $Zn^{2+}$ ions into the oral and oropharyngeal tissues is of particular benefit in reducing the duration of common colds, curing the common cold, treating common colds or common cold symptoms.

GENERAL BACKGROUND

The art of managing metallic ions in food products has received much attention by the food industry. Metallic ions of iron, copper and zinc can be present in some food products with adverse effects on food integrity. If they are allowed to remain in some food products even in low concentrations, such metallic ions can greatly reduce shelf life of some fats, oils and other foods that are subject to spoiling and oxidization. However, that $Zn^{2+}$ ions must be present in some medicinal oral compositions is new and is of importance in compositions intended for use in common cold treatment. Such application presents problems in preserving a pleasant taste of said compositions.

Chemical Sequestration of Metallic Ions

Sequestrants are chemicals that deactivate or stabilize these metallic ions by chemically tying up positively charged metal ions through chemical reactions to form stable, neutral or negatively charged complexes that do not adversely affect integrity or quality of such food products. Sequestrants are also known as sequestering agents, stabilizers, chelators, chelating agents and metal scavengers. Sequestrants help to establish, maintain, and enhance integrity of many food products. From a food manufacturing viewpoint, strong sequestrants serve to stabilize or enhance numerous properties identified with wholesome food including color, flavor and texture. Usually, sequestrants chemically react with metallic ions to form complexes which alter the properties and effects of metals in substrates. Many sequestrants employed in food production occur naturally in nature. Complexes of zinc either used in foods or found in foods include the chloride, propionate, butyrate, n-butyrate, beta-hydroxybutyrate, benzoate, formate and acetate. All have sufficiently low first stability constants (log $K_1=0$ to 1.0) that they exist essentially as 100% $Zn^{2+}$ ions at aqueous solution at pH 7.4; with zinc succinate, zinc gluconate and zinc sulfate, also used in foods, being slightly less ionizable. Many other complexes of zinc such as zinc citrate, zinc glycinate, zinc oxide, zinc tartarate, zinc orotate, zinc aspartate, zinc amino acid chelates and zinc carbonate are too tightly bound at pH 7.4 to release sufficient $Zn^{2+}$ ions to be useful as a source of orally absorbable $Zn^{2+}$ and are outside of this invention. However, said tightly bound zinc complexes are popular and readily available over-the-counter, but without efficacy against common cold duration, in commercial zinc lozenges as they have no objectionable taste and aftertaste properties. Other sweeteners, including saccharin, sorbitol, mannitol and a constituent of aspartame, phenylalanine, have also been shown to sequester metals. For sequestration, chelation, to occur two general conditions must be met: (a) ligands must have proper steric and electronic configuration in relation to metal ions being complexed and (b) the surrounding milieu (pH, ionic strength, solubility, etc.) must likewise be conducive to complex formation. That strong sequestration of metal ions is a desirable goal of food manufacturers is well known in the art.

Desirability of Weak Sequestration in Common Cold Treatment

The desirability of strongly sequestering metal ions in all cases must be challenged in view of the nature of some metal chelators relative to environments in which their use is intended. For example, use of zinc gluconate in throat lozenges, troches and similar oral means has been described as a method for reducing duration of common cold symptoms (U.S. Pat. No. 4,503,070, Mar. 5, 1985 and its reissue RE 33465, Nov. 27, 1990). In such usage, $Zn^{2+}$ ions are only weakly bound by the gluconate moiety. The first stability constant of zinc gluconate is log $K_1=1.70$. At oral tissue pH 7.4, zinc gluconate in aqueous solution releases 30% of its zinc as $Zn^{2+}$. Such $Zn^{2+}$ ions are readily available for those biochemical activities in oral and oropharyngeal mucous membranes at pH 7.4 that result in a reduction in duration of common cold symptoms.

Although the exact nature of biochemical activities of zinc ions in reducing duration of common colds remains to be determined, it is conclusive that zinc must be present as $Zn^{2+}$ ions. That $Zn^{2+}$ ions act to reduce common cold duration by an antiviral mechanism must be understood. Published articles, describe the in vitro antirhinoviral activity of $Zn^{2+}$ ions from highly ionizable zinc chloride and zinc acetate. Said articles include:

B. D. Korant, et al. (1974), "Zinc Ions Inhibit Replication of Rhinoviruses", *Nature,* 248:588–590.

B. D. Korant and B. E. Butterworth, (1976), "Inhibition by Zinc of Rhinovirus Protein Cleavage: Interaction of Zinc with Capsid Polypeptides", *Journal of Virology,* 18:298–306.

B. E. Butterworth, et al. (1976), "Replication of rhinoviruses", *Archives of Virology,* 51:169–189.

B. D. Korant, (1976), *Chemical Abstracts,* 85:76, Abst. No. 814y.

B. D. Korant, (1979), "Role of Cellular and Viral Proteases in the Processing of Picornavirus Proteins", in *The Molecular Biology of Picornaviruses,* pp. 149–173, R. Perez Bercoff, ed., Plenum Publishing.

B. D. Korant, (1979), "Inhibition of Viral Protein Cleavage", in *Design of Inhibitors of Viral Functions,* I. Gauri, ed., Academic Press.

V. J. Merluzzi et al., (1989), "Evaluation of Zinc Complexes on the Replication of Rhinovirus 2 In Vitro", *Research Communications in Chemical Pathology and Pharmacology,* 66:425–440.

Geist F. C., Bateman J. A., Hayden F. G. (1987), "In Vitro Activity of Zinc Salts against Human Rhinoviruses", *Antimicrobial Agents and Chemotherapy,* 31:622–624.

The Korant et al. and Butterworth et al. articles describe the antirhinoviral activity of $Zn^{2+}$ from zinc chloride and highly ionizable zinc compounds as being complete or nearly complete inhibition of viral replication at about 0.1 mMol, which is about 6.67 times normal zinc serum concentration in humans. The Merluzzi et al. article shows in FIG. 1 that $Zn^{2+}$ is as protective of rhinovirus infected monolayer cells as interferon. Merluzzi et al. show that the antirhinoviral activity of zinc complexes tested in the rhinovirus cytopathogenic effect (CPE) assay was directly related to the amount of unbound $Zn^{2+}$ ion available, and not to the total amount of zinc. The Geist et al. article demonstrates the antirhinoviral activity of $Zn^{2+}$ at concentrations of $Zn^{2+}$ of 0.1 mMol, but not for lower concentrations, and the toxicity of $Zn^{2+}$ at higher concentrations.

Other possible mechanisms for the effect of $Zn^{2+}$ on common colds are the mitogenic effect of $Zn^{2+}$ ions on human lymphocytes and interferon induction. Zinc chloride, a totally ionizable zinc compound, induces gamma-interferon at 0.05 to 0.5 mMol concentration (M. Salas and H. Kirchner, 1987, "Induction of Interferon-Gamma in human leukocyte cultures stimulated by $Zn^{2+}$", *Clinical Immunology and Immunopathology,* 45:139–142). Such concentration is essentially the same as that required for antirhinoviral effects.

Published articles show beneficial in vivo effects of zinc gluconate lozenges which release zinc ions against the duration and severity of common colds. Articles showing positive effects include:

G. A. Eby et al., (1984), "Reduction in Duration of Common Cold Symptoms by Zinc Gluconate Lozenges in a Double Blind Study", *Antimicrobial Agents and Chemotherapy,* 25:20–24.

W. Al-Nakib et al., (1987), "Prophylaxis and Treatment of Rhinovirus Colds with Zinc Gluconate Lozenges", *Journal of Antimicrobial Chemotherapy,* 20:893–901.

D. S. Smith et al., (1989), "Failure of Zinc Gluconate in Treatment of Acute Upper Respiratory Tract Infection", *Antimicrobial Agents and Chemotherapy,* 33:646–648.

Each article reported the effect of $Zn^{2+}$ from zinc gluconate, and each showed a marked reduction in duration of common cold symptoms which was totally dependent upon zinc ion availability (ZIA). The Eby et al. lozenges had a ZIA value of 100 which was more than twice the ZIA 43.9 value of the Al-Nakib lozenges and 4 times the ZIA 25 of the Smith lozenges. Careful analysis of results of these 3 studies show a 7 day, 4.8 day and 1.6 day reduction in duration of common colds, respectively, due to the different ZIA values of the lozenges. The lower ZIA values were attributed to faster dissolution rates and lower zinc ion concentration in both the Al-Nakib et al. and Smith et al. studies, while very bitter taste and lack of compliance with protocol (dosage reduced by half) also complicated the Smith et al. study. Bitterness of zinc gluconate lozenges is increased by 1 to 3 orders of magnitude if lozenges are not made either with: (a) no other soluble ingredients as was present in the Eby et al. study, or (b) no other solubles or carbohydrate sweeteners other than fructose as was present in the Al-nakib study.

Adverse Effects of Sequestration in Common cold Research

Conversely, in a similar 1987 study "Two Randomized Controlled Trials of Zinc Gluconate Lozenge Therapy of Experimentally Induced Rhinovirus Colds", *Antimicrobial Agents and Chemotherapy,* 31:1183–1187, by Barry M. Farr et al., citric acid, a strong zinc chelator, was used in lozenges in extramolar amounts sufficient to eliminate taste of zinc gluconate, resulting in no reduction in duration of common colds. The first stability constant of citric acid for zinc ions is generally accepted to be log $K_1=4.5$. In oral use in lozenge form, zinc gluconate rapidly ionizes. It is known in the art that if such occurs in the presence of sufficient amount of a chelator having a high stability constant for zinc ions such as equimolar or extramolar citric acid, a new, vastly stronger equilibrium replaces the weak association with gluconate which can eliminate the availability of metallic ions at pH 7.4. In the Farr et al. experiment such zinc citrate equilibrium resulted in neutral and negatively charged compounds having no bioavailability at normal oral tissue pH according to Berthon, May and Williams, *Journal of the Chemical Society, Dalton* 1978; 1433–1438. In the case of lozenges containing zinc gluconate with extramolar citric acid, soluble zinc citrate complexes were shown to be tasteless and were proposed to be sufficiently biologically available to be effective in reducing duration of common colds. However, with addition of extramolar citric acid, there occurs in saliva such powerful binding of zinc ions that neutral or negatively charged zinc species predominate. A near complete loss of positively charged $Zn^{2+}$ ions occurs in saliva at pH 4.3 and a complete loss of $Zn^{2+}$ ions occurs in oral tissues at pH 7.4. There is no metallic taste. No localized activity occurs, and no reduction in common cold duration occurs from zinc tightly bound by citrate.

Similarly, an article by R. M. Douglas, et al., entitled "Failure of Effervescent Zinc Acetate Lozenges to Alter the Course of Upper Respiratory Tract Infections in Australian Adults", published in *Antimicrobial Agents and Chemotherapy,* 31:1263–1265 shows the effects of adding other strong chelators. Strong effervescence was produced by reacting tartaric acid and sodium bicarbonate, and the lozenge base was mannitol according to a 1987 letter to R. M. Douglas, University of Adelaide from R. J. E. Williams of F. H. Faulding & Company, Adelaide, South Australia. Such addition resulted in strong effervescence and chelation of zinc to insoluble zinc carbonate and tightly bound zinc tartarate. Again, strong chelation resulted in lack of efficacy against common colds.

Similarly, glycine, a strong zinc chelator (first stability constant log $K_1=4.8$), added to zing gluconate in candy lozenges in the manner according to U.S. Pat. No. 4,684,528 reduces the amount of $Zn^{2+}$ available at salivary pH 5.0 to about 20% of the available zinc, and at pH 6.4 and above there is no $Zn^{2+}$ present. Only neutral and negatively charged zinc glycinate species are found at oral tissue pH 7.4 according to simulation calculations and figure by Guy Berthon, a solution chemist at INSERM U305 in Toulouse, France. Consequently, there is no reduction in the duration of common colds during the first 4 or 5 days of treatment relative to placebo (Godfrey et al., J. Internation. Med. Res., 1992;20:234) and only the astringent properties of $Zn^{2+}$ at salivary pH appear opperative which seem to help dry up colds about a day faster than placebo after the 4th or 5th day of treatment. U.S. Pat. No. 4,684,528 failed to teach a method that was non-toxic, as glycine was recinded from the U.S. Food and Drug Administration list of Generally Recognized as Safe (GRAS) food ingredients in CFR Title 21 § 121.12 in 1971 and remained rescinded for use in foods and non-prescription drugs in CFR Title 21 § 170.50 since then.

Toxicity of Zinc Compounds and $Zn^{2+}$ Ions

In vitro, it is generally recognized that elevated extracellular $Zn^{2+}$ ions are beneficial and elevated intracellular zinc (over 0.0001 to 0.001 mM) is cytotoxic [Pasternak, BioAssays, 1987;6:14; and Pasternak, Bioscience Reports, 1987;7:81–91.], although recently some have suggested that slightly elevated extracellular zinc is cytotoxic. For example, cell rounding and refractile changes occur at about 0.1 mM $Zn^{2+}$ (Geist et al., 1987; Merluzzi et al., 1989). Importantly, cell death occurred at much lower concentrations for most lipophilic and strongly chelated zinc complexes. Others, including those familiar with the unique appearance of the astringent action of $Zn^{2+}$ on cell plasma membranes, found that extracellular $Zn^{2+}$ is a newly recognized host defense [Bashford C. L. et al., J. Bio. Chem., 1986;261:9300; Bashford C. L. et al., J. Immunol., 1988; 141:3965; Bashford C. L. et al., J. Membrane Biol., 1988;103:79; Chvapil M., Med. Clin. North Amer., 1976;60:799]. Hydrated $Zn^{2+}$ ions protect cell plasma membranes against damage induced by cytotoxic agents of environmental origin long enough for other defense mechanisms to be brought into play, with protective effects increasing up to 1 mMol in vitro, although cytotoxicity occurs above 1 mMol. At non-toxic concentrations elevated extracellular $Zn^{2+}$ ions inhibit, and specifically do not promote, an influx of intracellular zinc, but lipophilic complexes of zinc pass into the interior of cells where they are toxic, causing cell damage and cell death, in direct relationship to their degree of lipophilicity.

Hydrated $Zn^{2+}$ ions are known to be astringent and non-lipophilic and do not pass through the cell plasma membrane. For $Zn^{2+}$ ions rounding and refractile changes result from its astringent, protective action on cell membranes, and not from cytotoxicity. All astringents, including $Zn^{2+}$, are locally applied protein precipitants that have such low cell penetrability that action is essentially limited to cell surfaces and interstitial spaces (contraction, rounding, wrinkling and blanching in vitro) [Osol A., Remington's Pharmaceutical Sciences, 16th Edition, (1980)., Mack Publishing Company, Easton, page 720]. Permeability of cell membranes is reduced, but cells remain viable. Also, astringents harden the cement substance of capillary epithelium so that pathological transcapillary movement of plasma protein is inhibited and local edema, inflammation and exudation are thereby reduced. Additionally, they reduce mucus and other secretions in tissues containing goblet cells and other secretory cells, so that affected areas become drier. However, excessively high concentrations of astringents including $Zn^{2+}$ cause irritation and cell damage.

Recommended concentrations of zinc acetate for use as an external or skin topical astringent are 0.2 to 2.0% (9 to 90 mM $Zn^{2+}$) (Osol, 1980). However, the oral and oropharyngeal tissues have much greater $Zn^{2+}$ absorption characteristics than skin and Osol's recommended concentrations for skin application consequently are not applicable to the interior of the mouth. For example, the oral and oropharyngeal tissues have an electrical resistance of about 9,000 ohms, while the electrical resistance of the skin is essentially infinite. The present inventor found that there is a biologically closed electrical circuit (BCEC) between the mouth and the nose which promotes absorption of $Zn^{2+}$ between the oral mucosal cells. $Zn^{2+}$ passes between cells through interepithelial spaces called stomata, pores or leaky junctions of the oral and oropharyngeal mucosal membranes with flow of $Zn^{2+}$ being directed from the mouth toward the nose. The circuit carries about 100 millivolts with a readily detectable current. For example, reversing ohm meter leads between the mouth and the nose changes resistance readings by about 10,000 ohms. There is no electrical stimulus for absorption of $Zn^{2+}$ across the skin and concentrations of zinc acetate and other ionic substances can be much higher without tissue irritation or cytotoxicity. The mouth-nose BCEC is believed responsible for absence of efficacy of $Zn^{2+}$ against the duration of common colds when it is applied as nose drops or nasal sprays.

Contrary to in vitro reports cited above of general toxicity at 1 mMol, no evidence of toxicity from $Zn^{2+}$ lozenges having non-toxic ligands exists, other than transitory and mild oral irritation on occasion; even though lozenges used by Eby et al. in 1984 produced salivary zinc concentrations of 7.4 mM. The highest non-toxic salivary zinc concentration from zinc acetate lozenges recorded is 21 mM. Rather than being toxic to oral tissues, they are associated with accelerated patient recovery. When said compositions are applied to oral and oropharyngeal membranes of a human, they are non-toxic, meaning that there is no evidence that they are absorbed into the interior of cells in a manner which causes significant cytotoxicity at the concentrations used, which is contrary to in vitro findings. Oral irritation and strong taste sensation from $Zn^{2+}$ lozenges are much less apparent in patients with colds than without colds, perhaps due to increased oral membrane permeability in patients having colds compared to patients without colds.

Complexes of zinc including the chloride, propionate, butyrate, n-butyrate, beta-hydroxybutyrate, benzoate, formate and acetate have sufficiently low first stability constants (Log $K_1=0$ to 1.0) that they exist as 100% $Zn^{2+}$ ions at aqueous solution at pH 7.4. Zinc succinate, zinc gluconate and zinc sulfate are slightly less ionizable but are still considered to be highly ionizable zinc compounds. All highly soluble, highly ionizable zinc compounds having non-toxic ligands having a very low first stability constant (less than about log $K_1 = 2$, and especially less than about log $K_1 = 1$) are believed non-toxic from $Zn^{2+}$ at the concentrations used in compositions described in present invention.

From the above observations, it is shown that: (a) hydrated $Zn^{2+}$ ions from lozenges do not enter or damage cells, while lipophilic and more tightly complexed zinc compounds promote cellular damage and cellular death by their ability to cross cell plasma membranes; (b) beneficial effects of concentrated $Zn^{2+}$ ions occur exclusively at the cell membrane; and (c) oral absorption of topical $Zn^{2+}$ ions through the oral mucosal membrane relies upon a non-lipophilic mechanism. The oral irritation from zinc gluconate lozenges may be due to intracellular absorption of neutral charged zinc gluconate which is present along with $Zn^{2+}$ at pH 7.4.

Effect of Zinc Ion Availability (ZIA)

Analyses of the previously cited studies showed that zinc gluconate lozenges containing no other zinc complexing agents reduced the severity and duration of common colds in a ZIA-dependent manner with minor oral irritation. Responses to treatment followed Fick's law of membrane permeability. Responses were directly related to zinc ion availability (ZIA) which is dependent upon the amount of $Zn^{2+}$ available from lozenges at oral tissue pH 7.4, the duration of oral residency of the lozenges in the mouth (dissolution time of lozenges), the amount of saliva produced, initial $Zn^{2+}$ salivary concentration and the number of dosages given per day. Surprisingly and unexpectedly, results against common cold duration from zinc lozenges where the ligand was a strong chelator which produced negatively charged zinc species at oral tissue pH 7.4 (citrate, tartarate and carbonate) resulted in worsened and lengthened common colds compared to placebo, while lozenges carrying neutral charged zinc produced no change in common cold duration from placebo. Analyses of the above cited reports with respect to zinc ion availability as a means to reduce common colds and to predict efficacy of zinc lozenges are available in "The Zinc Lozenge and Common Cold Story" in *Handbook on Metal-Ligand Interaction of Biological Fluids*, edited by Guy Berthon of INSERM U305 in France, published in 1994 by Marcel Deckker, Inc. in New York, while a more detailed review of the effects of positively, neutral and negatively charged zinc on the duration of common colds is in a 1993 book entitled *Handbook for Curing the Common Cold (The Zinc Lozenge Story)* available from the present inventor.

Flavor Stability of Compositions Containing Highly Ionizable Zinc Compounds

There are additional requirements of composition ingredients. For product shelf-life, all ingredients must not adversely affect the taste of the composition. Said ingredients so constituted into said compositions must not degrade in taste when aged or thermally stressed. Compositions must be non-toxic, thermally, chemically and flavor stable under all normal and near normal storage conditions over long periods of time. All ingredients should be inexpensive, readily available and either demonstrated safe or Generally Regarded As Safe (GRAS).

This inventor conducted multi-year stability tests of numerous non-toxic, pleasant tasting, flavor-masked zinc compositions containing highly ionizable zinc compounds. All available sweet pharmaceutically acceptable tablet bases including sugars such as sucrose, dextrose, fructose, lactose, Mendell's Sugartab ®, Emdex ®, Sweetrex ®; sugar-alcohols such as mannitol, sorbitol, and xylitol, and other commercial products specifically designed for pharmaceutical tablet manufacturing were tested with numerous zinc compounds with and without flavor-masks. Compositions were exposed to seasonal temperatures reaching 45 to 55 C. degrees during summer months for long term storage testing and to similar temperatures in accelerated aging tests. This inventor found that:

Compressed tablets containing zinc gluconate in various tablet bases of sucrose, dextrose, lactose, maltodextrin, xylitol, sorbitol, mannitol and all direct compression tableting compositions developed exceedingly bitter, very long lasting (24 to 60 hours), seriously objectionable tastes and aftertastes after storage for a few days to a few months. Bitterness was 1 to 3 orders of magnitude greater than the bitterness from any other highly ionizable zinc compound tested.

Compressed tablets containing zinc gluconate in a tablet base of ground fructose agglomerated with polyethylene glycol 8000 (PEG-8000) to about 10%, did not develop the seriously objectionable taste and aftertaste for a storage period of over one-year, although they continued to have the mild, essentially non-objectionable zinc gluconate taste observed in the Al-Nakib et al. lozenges which were prepared with fructose bound by Methocel.

Surprisingly, and unexpectedly, other highly ionizable zinc compounds including the chloride, propionate, butyrate, n-butyrate, beta-hydroxybutyrate, benzoate, formate, acetate, succinate and sulfate in a tablet base of either one or more crystalline fructose, dextrose and agglomerated sucrose in various ratios in compressed tablets, retained a pleasant sweet taste, and had no objectionable aftertaste typical of zinc gluconate after a two-year storage period. Surprisingly, and unexpectedly, these highly ionizable zinc compounds in lozenges or tablets do not produce the zinc gluconate-like exceedingly bitter, very long lasting and seriously objectionable aftertaste upon aging in the presence of fructose, sucrose or other sweeteners. All highly ionizable zinc compounds in solid forms have taste and aftertaste between 1 and 3 orders of magnitude less objectionable than similar lozenges having zinc gluconate. However, some compositions have a mild flavor of the ligand which may be controlled or eliminated with added saccharin and flavoring. Each lozenge composition tested having highly soluble, highly ionizable zinc compounds when formulated as ZIA 100 lozenges reduces the duration of common colds identically to those ZIA 100 zinc gluconate lozenges tested by Eby et al. in 1984.

Surprisingly and unexpectedly, pleasant tasting highly ionizable zinc compounds including the chloride, propionate, butyrate, n-butyrate, beta-hydroxybutyrate, benzoate, formate, acetate, succinate and sulfate in hard and soft candy lozenges, chewing gums, toothpaste's, mouth rinses, gargles, syrups, powders, tablets, sprays and so forth tested were also pleasantly flavored without objectionable zinc gluconate-like exceedingly bitter, very long lasting and seriously objectionable aftertaste with addition of those highly ionizable zinc compounds to existing products. However, each has a mild flavor of the ligand which is controlled with saccharin and flavoring. Each composition having highly soluble, highly ionizable zinc compounds when formulated as ZIA 100 compositions reduce the duration of common colds identically to those ZIA 100 zinc gluconate lozenges tested by Eby et al. in 1984.

When the pharmaceutically acceptable carrier was sweet or was a sugar, the taste of the composition was best. Although sweetness appears to flavor-mask highly ionizable zinc compound tastes, there is no apparent explanation for the lack of extreme bitterness and seriously objectionable aftertaste from these compounds normally associated with zinc gluconate. Until this disclosure, the previously believed objectionable taste of zinc lozenges was attributed to $Zn^{2+}$ when mixed with any tablet-base sweetener other than fructose. This inventor found that $Zn^{2+}$ has no taste of its own other than astringency, and the taste of zinc complexes are primarily the result of the taste of ligands of zinc reacting with other composition ingredients. Small amounts of saccharin were beneficial in improving sweetness when marginally sweet pharmaceutically acceptable carriers such as dextrose, lactose or maltose were used. However, excessive amounts of saccharin (over 50 mg) often resulted in a bitter saccharin taste.

A generalized characterization of said findings shows that solid compositions containing any highly ionizable zinc compound other than zinc gluconate provide a highly significant improvement in taste over solid compositions containing zinc gluconate. Several pleasant tasting commercial mouth washes such as Lavoris use zinc chloride and saccharin without objectionable taste and aftertaste, primarily because they are never allowed to remain in the mouth for extended times. However, no solid oral compositions using zinc chloride are known to have been demonstrated by others to have a pleasant taste and without objectionable aftertaste.

The surprising and unexpected observation that non-toxic, highly ionizable solid oral zinc compositions may be prepared with sucrose, fructose, and other sugars with or without other ingredients without loss of flavor, sweetness or degradation from thermal and storage stresses and without added flavor-masks is a significant original, surprising and unexpected finding new to the art. The showing that flavor enhancements to highly ionizable zinc compounds in solid oral compositions occur with sweet pharmaceutically acceptable carriers or added super sweeteners such as saccharin is significant, surprising and unexpected, particularly when one realizes that solid compositions do not need to be perceived as sweet to exclude objectionable taste and aftertaste previously, but erroneously, attributed to $Zn^{2+}$.

Flavor-Mask Findings of Others

U.S. Pat. No. 4,684,528 discloses a slow-release candy compositions, comprising a hard candy base (hard boiled sucrose and corn syrup), zinc gluconate, or other zinc compounds, and an amino acid having a molar ratio of said amino acid to zinc of about 2 to 20, and various other oral compositions containing zinc compounds and certain amino acids. Such compositions can be flavor-masked by glycine and certain other amino acids. Importantly, said amino-acid flavor-mask patent teaches that ionizable zinc compound formulations of hard candy without glycine have a sharp, undesirable taste and an unpleasant aftertaste, which is directly contrary to the findings of the present inventor. Glycine is not considered by the U.S. FDA to be a safe food ingredient. Glycine was first recinded from the list of Generally Regarded As Safe (GRAS) substances by the U.S. Food and Drug Administration in CFR Title 21 § 121.12 as revised on Jan. 1, 1971 and has remainded rescinded in CFR Title 21 § 170.50 each year since then. Additionally it has recently been demonstrated by solution chemists at INSERM in France, that extramolar glycine flavor-masked zinc compositions release no $Zn^{2+}$ at oral tissue pH 7.4 and therefore cannot be expected to produce a significant early reduction in the duration of common colds.

Anethole has been discovered to be an aromatic flavor-mask and aftertaste mask for all soluble and ionizable zinc compounds and is disclosed and claimed by U.S. Pat. No. 5,002,970, issued Mar. 26, 1991. All compositions flavor-masked with anethole retain their original ZIA values and the flavor of anethole, to which some persons object.

The Current Need

There is an important, current need to develop improved, pleasant-tasting $Zn^{2+}$ releasing oral compositions that are non-toxic, thermally, chemically and flavor stable that do not contain added flavor-masks such as amino acids or anethole. Lozenges and other means having a pleasant taste that introduce $Zn^{2+}$ ions slowly over a prolonged period of time into oral and oropharyngeal mucous membranes so as to increase their zinc ion availability (ZIA) value are needed primarily for treatment of common colds, common cold symptoms, acute upper respiratory allergies, and nutritional supplementation. Common cold symptoms include acute nasal drainage, nasal congestion, headache, fever, myalgia, sneezing, sore throat, cough, hoarseness and sinusitis. In as much as serious mistakes taken from the prior art of taste management of $Zn^{2+}$ releasing solid zinc compounds have been made, particularly in the invention of zinc lozenges for treating common colds; it is apparent that errors of the prior art must receive attention. A new improved way of preventing toxicity and eliminating objectionable taste and aftertaste of zinc compositions releasing essentially 100% of their zinc as $Zn^{2+}$ is needed.

PRIMARY OBJECTIVE AND GENERAL DESCRIPTION OF INVENTION

Accordingly, it is a primary objective of this invention to disclose and claim improved solid oral zinc compositions that are non-toxic, thermally, chemically, and flavor stable. Said compositions shall be devoid of the objectionable flavor and aftertaste commonly associated with oral zinc gluconate compositions. Said compositions shall be intended to release $Zn^{2+}$ ions into oral and oropharyngeal mucous membranes for local absorption and movement through BCECs into the nose. Said compositions are primarily intended to be used to reduce duration of common colds or their symptoms, management of upper respiratory allergy, for nutritional support or for related purposes. Said compositions shall contain one or more highly ionizable zinc compounds, excluding zinc gluconate, which have been discovered by this inventor to be non-toxic and not to have an objectionable taste or aftertaste when properly formulated. These primary objectives and other objectives of this invention will be found apparent from the following general description and detailed examples.

Compositions Containing Highly Ionizable Zinc Compounds Generally

This inventor discloses and claims non-toxic, flavor-stable, pleasant tasting solid oral compositions specifically containing highly ionizable zinc compounds and pharmaceutically acceptable carriers for use primarily in human common cold treatment, upper respiratory allergy management and for nutritional support. Said compositions are intended to be dissolved in the mouth, masticated or otherwise used in the mouth to release $Zn^{2+}$ ions into the tissues of the oral cavity and oropharyngeal tissues of humans. Said highly ionizable zinc compounds are to be slowly and uniformly released by aqueous dissolution of solid ingredients within said solid oral composition, as said compositions are held or retained in the mouth. Saliva, generated by the person orally dissolving said composition, is the usual source of said aqueous solvent. Ideal oral cavity retention time periods are 30 minutes per application or use of composition. Soft candy and chewing gums are to release highly ionizable zinc compounds slowly over a sustained period of time.

Said highly ionizable zinc compositions are believed non-toxic as they release essentially 100% of their zinc as $Zn^{2+}$ at oral tissue pH 7.4 and at lower pit values. $Zn^{2+}$ is not believed to be absorbed into the interior of cells, and $Zn^{2+}$ exerts its beneficial effects solely on the cell membrane, perhaps by sealing the membranes so that virally infected cells do not release theft viruses extracellularly. Lipophilic complexes of zinc and neutral charged zinc species at pH 7.4 may be cytotoxic when absorbed into cells which may worsen common colds through increased tissue damage, particularly oral tissue damage. Negatively charged zinc complexes at pH 7.4 may also be toxic and may similarly increase the duration and severity of colds. Such may have been the cause of increased severity and duration of colds in the Farr et al 1987 study and the Douglas et al. 1987 study which released negatively charged zinc and neutral zinc complexes.

Invented compositions of highly ionizable zinc compounds are stable, meaning that negligible degradation in flavor, appearance or chemistry occured in tested compositions under extended multi-year storage in normal and near normal temperature conditions while sealed in air-tight, opaque containers. Compositions of said highly ionizable zinc compounds are non-toxic, pleasant tasting and have a pleasant aftertaste, generally defined by the ligand, the added flavors, the pharmaceutically acceptable carrier, or by added super sweeteners such as saccharin. Said compositions are an improvement upon a slow-release candy composition comprising a hard candy base, zinc gluconate and an amino acid, as said sweet compositions of the present invention exclude zinc gluconate and amino acids; and whereby said compositions are improvements upon a medicinal composition for release of zinc ions consisting essentially of a suitable pharmaceutical carrier, zinc compounds and anethole; as present composition excludes anethole.

As discovered from said thermal and aging stability studies, compositions are nontoxic, usually without an objectionable taste or aftertaste even without an added flavor-mask. Compositions are non-toxic, chemically, thermally and flavor stable with no increase in bitterness under high summer-time temperature conditions over multi-year periods of time. This invention primarily discloses and claims the discovery of non-toxic, pleasant tasting and aftertaste-free compositions of highly ionizable zinc compounds dispersed in a consumable pharmaceutically acceptable carrier that reduce the duration of common colds. By necessity to clearly and more fully describe said compositions, said inventive compositions include:

Oral compositions containing highly ionizable zinc compounds in any pharmaceutically acceptable carrier such as fructose, Mendell's Sugartab ®, Sweetrex ® or Emdex ®, sucrose, dextrose, maltose, lactose, sweetened water and the like, singularly or in combination, with following pharmaceutical necessities included singularly or in combination, as desired:

tablet binders for compressed tablets, lozenges and troches including polyethylene glycol-6000 or 8000, flavor oils such as peppermint, methyl salicylate, menthol and eucalyptol excluding anethole, as disclosed by U.S. Pat. No. 5,002,970.

flavor oil stabilizers, including spray driers and cyclodextrins, coloring agents and dyes, glidants, including silica gel, tablet lubricants, including magnesium stearate, other necessities excluding amino acids as disclosed in U.S. Pat. No. 4,684,528;

and with the following medicinal additives included as desired or necessary:

antiviral agents, including antirhinoviral agents, antimycoplasmal agents, antibiotics, nasal decongestants, antihistamines, antinausea agents, analgesics, cough relievers, dental desensitizers, saliva inhibitors, vitamins, including ascorbic acid, minerals, other than zinc, and other medicinal agents and nutritional supplements either directly incorporated within compositions or chemically isolated through techniques including micro-encapsulated and inclusion within cyclodextrins. Micro-encapsulation with insoluble porous membranes providing a time release capability for ingredients that might interfere with release of zinc ions or adversely affect taste of composition is anticipated.

Such compositions include solid forms such as tablets, troches, lozenges and powders; chewable forms such as chewing gums and soft candies; and liquid forms such as syrups, mouth washes and sprays. When said compositions are applied to oral and oropharyngeal membranes of a human, they are non-toxic, meaning that they are not absorbed into cells in a manner which causes cytotoxicity at the concentrations used in the oral composition, palatable, without undesirable taste or unpleasant aftertaste, yet they allow oral and oropharyngeal absorption of $Zn^{2+}$ ions. When compositions are to be used to treat common colds, reduce the duration of common colds or cure common colds, said pharmaceutical necessities and medicinal additives shall not be present in sufficient quantities to impair the beneficial action of $Zn^{2+}$ on the duration of common colds or they shall be sealed through micro-encapsulation.

Highly Ionizable Zinc Compounds

For purpose of this invention highly ionizable zinc compounds include all highly soluble, non-toxic inorganic and organic complexes of zinc excluding zinc gluconate having a first stability constant less than about log $K_1=2$. Inorganic highly ionizable complexes of zinc include zinc chloride (log $K_1=0.0$) and zinc sulfate, both of which are Generally Recognized As Safe (GRAS) as well as other inorganic zinc complexes having a first stability constant of zinc of less than about log $K_1=2$. Organic highly ionizable zinc complexes having a first stability constant of less than log $K_1=1.0$ are preferred and include zinc propionate, zinc butyrate, zinc n-butyrate, zinc beta-hydroxybutyrate, zinc benzoate, zinc formate and zinc acetate. Said preferred zinc complexes all have sufficiently low first stability constants (log $K_1=0$ to 1) that zinc exists essentially as 100% $Zn^{2+}$ ions at aqueous solution at pH 7.4. Zinc succinate and zinc sulfate are slightly less ionizable and are also preferred complexes of zinc.

Although zinc gluconate is the best known source of $Zn^{2+}$ ions in lozenges for treating common colds, highly soluble, highly ionizable zinc compounds other than zinc gluconate merit special attention. For purposes of this invention, zinc lozenges for treating common colds, curing common colds or reducing the duration of common colds contain between about 0.2 and 500 mg zinc and more often contain about 2 to 50 mg of zinc and most often contain about 10 to 23 mg zinc from a highly ionizable zinc compound excluding zinc gluconate dispersed in about 1 to 15 grams of a pharmaceutically acceptable carrier, and preferably a sweet pharmaceutically acceptable carrier. Highly soluble, highly ionizable zinc compounds offers improved, unexpected characteristics over zinc gluconate that require close attention.

Surprising and Unexpected Taste Characteristics

Undiluted highly ionizable zinc compounds have dreadful, vile tastes and some have sharp disagreeable odors. Most important, surprising, totally unexpected, and patently unique; any non-toxic highly ionizable zinc compound other than zinc gluconate sufficiently diluted with any pharmaceutically acceptable carrier, such as sweetened water, fructose, sucrose, dextrose, starch, lactose, other sugars or other dilutants, has neither the seriously offensive taste nor the long lasting 24 to 60 hour bitter and offensive aftertaste like that present with zinc gluconate when said compositions are retained in the oral cavity of a human for sustained periods of time (defined as 5 to 30 minutes or more). Highly ionizable zinc compounds may be sufficiently diluted, yet sufficiently concentrated to be of utility against common colds when applied over such extended time. Properly prepared compositions have a pleasant taste and pleasant aftertaste. All common cold orally absorbed compositions (whether containing $Zn^{2+}$ or other antirhinoviral agents) are required to be slowly and uniformly released in a sustained manner into the oral cavity as said composition is being orally consumed or masticated and, said compositions must be non-toxic, stable and have a pleasant taste and aftertaste during composition dissolution. Sustained application of $Zn^{2+}$ ions (defined as 5 to 30 minutes or longer per application) to the interior of the mouth including the tongue, oral cavity, throat and oropharyngeal surfaces from a palatable composition releasing a 1 to 50 millimolar concentration of $Zn^{2+}$, and preferably about 5 to 15 millimolar concentration, and more preferably about 7 to 10 millimolar concentration for preservation of best taste is necessary in order to be effective in reducing the duration of common colds. This present inventor also discovered that the objectionable taste of highly ionizable zinc compounds is eliminated with addition of consumable, pharmaceutically acceptable carriers such as fructose, sucrose, dextrose and other sugars and sweeteners; with or without added super sweeteners like saccharin and various flavors; all of which is directly contrary to teachings of U.S. Pat. No. 4,684,528.

Fructose, Sucrose and Dextrose as Pharmaceutical Carriers

Fructose is the sweetest of the natural sugars. It is a component of sucrose, a disaccharide, and is an isomer of dextrose, all of which are sugars. Neither fructose, sucrose nor dextrose are believed to chelate zinc in a way that would detract from its utility in treating common colds. The first stability constant of dextrose for $Zn^{2+}$ is log $K_1=0.01$ [Briggs J. et al. (1981), *Carbohydrate Research*, 97:181]. It is surprising and unexpected that fructose does not visibly react, change color or form bitter compounds with highly ionizable zinc compounds at higher ambient temperatures as this monosaccharide is a polyhydroxy ketone and is usually considered highly reactive. On the other hand, dextrose, a polyhydroxy aldehyde is normally considered to be an inert monosaccharide. Dextrose reacts with zinc gluconate over time to form extremely bitter complexes, but not with other highly ionizable zinc compounds tested. Various sweet tasting commercial tablet bases having a modified sugar tablet base produce bitter zinc gluconate lozenges after lozenges age for a few weeks, particularly when exposed to high summer temperatures. However, various sugar tablet bases do not become bitter in lozenges when used with those highly ionizable zinc compounds tested by present inventor in lozenges or tablets, regardless of time or temperature.

Favored Compositions of Fructose and Dextrose with Highly Ionizable Zinc Compounds It can now be revealed that preference is given to compositions of highly ionizable zinc compounds over zinc gluconate in a fructose and agglomerated dextrose based carrier over other sweet carriers. Favored formulation is any highly ionizable zinc compound other than zinc gluconate having a first stability constant of log $K_1=$ from less than 0 to about 2, and preferably from less than 0 to about 1, in lozenges having a carrier of fructose mixed with agglomerated dextrose. Tablets with crystalline fructose as a carrier could be bound by Mendell's Emdex® at about one-half the weight of crystalline fructose without tablet capping. Generally lozenges are made in a 2 to 6 gram size to allow a suitable dissolution rate for lozenges. Dissolution time should be about 15 minutes in water bath testers at 37 C. degrees or about 30 minutes when orally dissolved as lozenges for treatment of common colds, common cold symptoms, curing common colds or reducing the duration of common colds. Greatest efficacy occurs when saliva generation is lowest, thus raising $Zn^{2+}$ molar concentration in the oral cavity, suggesting utility for incorporating saliva inhibitors into compositions. Increased sweetness and strong flavorings increase salivation which decreases $Zn^{2+}$ concentration and efficacy.

Smaller and larger lozenges from 0.1 up to 15 grams are anticipated by this invention.

Compressed Tablet Compositions

Lozenges, tablets and troches in this invention are essentially the same, but may differ in shape, size and manufacturing technique. Since fructose is sweeter than sucrose and other sugars, it is preferred for use in direct compression of lozenges containing highly ionizable zinc compounds. Fructose may be processed for direct compression of tablets, troches and lozenges by incorporation of a tablet binder such as PEG-8000, perhaps using fluid bed agglomeration techniques wherein PEG has been diluted with water and the ground fructose crystals are agglomerated with PEG. To make directly compressible lozenges, add highly ionizable zinc compounds to PEG-8000 processed fructose; or add highly ionizable zinc compounds excluding zinc gluconate to crystalline fructose and commercially available, sweet, direct compression products such as Mendell's Sugar-tab ®, Sweetrex ®, or Emdex ®. Add saccharin if desired, flavors as desired, glidants such as silica gel as needed, and lubricants such as magnesium stearate as needed. Mixture should be kept dry and tableted soon after mixing. Ingredients are mixed and directly compressed into lozenges, tablets or troches using conventional pharmaceutical mixing and tableting equipment. Compressive force must be sufficient to produce maximum hardness throughout the lozenges to preserve the dissolution rate and maximum efficacy of lozenges in treating common colds or their symptoms, shortening the duration of common colds or curing common colds. Dissolution should occur over a sustained period of time, that being 5 to 30 minutes or more and preferably about 20 to 30 minutes. Store compositions in air tight containers in a cool dark place. If heated to high summer-time room temperatures, compositions, when properly prepared and sealed, are pleasantly flavored, do not turn brown over time and do not have a bitter aftertaste. Although added ingredients are not believed necessary to present a pleasantly flavored composition having no zinc aftertaste, addition of super sweeteners, such as saccharin is anticipated to improve the flavor of the basic composition and added pharmaceutical necessities and medicinal additives.

Liquid Compositions

Highly ionizable zinc compounds with a pleasant tasting, sweet, pharmaceutically acceptable carrier may be prepared in any liquid form such as syrups, mouth washes or sprays with water or other liquids for repeated delivery of concentrated highly ionizable zinc compounds excluding zinc gluconate to oral and oropharyngeal mucous membranes over a sustained period of time, that being 5 to 30 minutes or more and preferably about 20 to 30 minutes, so as to permit a prolonged contact by highly ionizable zinc compounds upon mouth and throat tissues. Said invention differs from zinc chloride mouth washes commercially available as present invention is to be retained in the oral cavity for much longer time than presently available mouth washes to effectively reduce the duration of common colds, treat common colds or cure common colds.

Soft Compositions

Highly ionizable zinc compounds in chewable compositions such as soft candy, gum drop, liquid filled candies, chewing gum base and dental supplies, such as tooth pastes and mouth washes, may be prepared by adding highly ionizable zinc compounds excluding zinc gluconate and sweeteners including fructose, sucrose and saccharin to them as needed. To obtain efficacy against the duration of common colds, to cure common colds or to treat common colds, said soft composition are retained in the mouth over a sustained period of time, that being 5 to 30 minutes or more and preferably about 20 to 30 minutes.

Super Sweeteners

Various super sweeteners including saccharin, aspartame, cyclamates, acesulfame K, neohesperidin dihydrochalcone and other super sweeteners may be added to the carrier in amounts sufficiently low so as not to chemically react with zinc to a therapeutically significant amount of $Zn^{2+}$. Preference is given to sodium saccharin, about 1 to 14 mg per 23 mg zinc, as additive super sweetener. Above 50 mg saccharin, compositions may have a bitter saccharin taste and aftertaste.

Flavors

Many flavorings can be added to impart their own flavor including but not restricted to peppermint, peppermint-menthol, eucalyptol, wintergreen, licorice, clove, cinnamon, spearmint, cherry, lemon, orange, lime, menthol and various combinations. Preference is given to peppermint (Bell #113.042) flavor plated onto silica gel for trueness of flavor and multi-year stability.

Stabilized Flavors

Some flavor oils may not be stable in long-term storage with highly ionizable zinc compounds in lozenges, and must be prevented from contacting zinc, evaporating and degrading generally. In lozenges and other dry solid compositions, flavors may be stabilized by spray drying with National Starch's N-Lok or other modified starches, or included within cyclodextrins, and/or coated with PEG 6000 or 8000. Inclusion of flavor oils within cyclodextrins results in essentially complete long-term thermal, oxidative and photo-decomposition stability. Of particular interest, inclusion results in protection against flavor oil degradation and oxidization otherwise accelerated by heat, light and metal salts. Spray dry flavors must not include acacia, and other vegetable gums that are powerful zinc chelators. Highly ionizable zinc compounds excluding zinc gluconate may be coated with PEG 6000, 8000 or higher molecular weight PEG or included within cyclodextrins to prevent contact of zinc with flavors. However, peppermint oil (Bell #113.042) plated onto silica gel (Siloid 244FP) is stable with no loss of flavor or aroma for at least two years in directly compressed highly ionizable zinc compounds lozenges in sealed amber glass bottles, and presumably any air-tight, opaque container.

Pharmaceutically Acceptable Carriers

Without regard to desirability of ingredients or intended use of compositions, a more complete list of sweet, consumable, pharmaceutically acceptable carriers includes but is not limited to: (a) carbohydrates including fructose, sucrose, sugar, dextrose, starch, lactose, maltose, maltodextrins, corn syrup solids, honey solids, commercial tablet compositions including Emdex ®, Mor-Rex ®, Royal-T ®, Di-Pac ®, Sugar-Tab ®, Sweet-Rex ®, New-Tab ®, (b) sugar alcohols including mannitol, sorbitol, xylitol, and (c) various relatively insoluble excipients including dicalcium phosphate, calcium sulfate, calcium carbonate, microcrystalline cellulose and other pharmaceutical tableting ingredients. Pharmaceutically acceptable carriers for compositions to be used for treating common colds by release of zinc ions in the oral cavity generally include 5 above, but preference is given to carriers other than the sugar-alcohols and insoluble ingredients because they lack sufficient sweetness and may adversely affect mouth-feel.

Undesirable Ingredients for Treating Common Colds

Highly ionizable zinc compounds in compositions for treating common colds must exclude positively-charged zinc ($Zn^{2+}$) ion-depleting ingredients and other incompatibles. Acacia, super sweeteners, citric acid, tartaric acid and other food acids, lake colors, alkalis and their carbonates, oxalates, phosphates, sulfides, lime water, and vegetable decoctions are considered incompatible with highly ionizable zinc compounds; and may cause compositions to be flavor unstable or cause a loss of efficacy against common colds or both. $Zn^{2+}$ ion depleting chelators must not be added in chemically significant amounts even if they are physically isolated from highly ionizable zinc compounds within compositions.

Examples of Invented Compositions

The following examples will serve to further illustrate, but not to limit, the present invention. Highly ionizable zinc compounds for purposes of the present invention are selected from the group of zinc compounds excluding zinc gluconate that have non-toxic ligands and have a first stability constant less than about log $K_1=2$. The preferred highly ionized complexes of zinc suitable for use in zinc lozenges include zinc chloride, zinc propionate, zinc butyrate, zinc n-butyrate, zinc beta-hydroxybutyrate, zinc benzoate, zinc formate, zinc acetate and all other non-toxic zinc complexes having very low first stability constants (log $K_1=$less than 0 to 1) so that they exist essentially as 100% $Zn^{2+}$ ions in aqueous solution at pH 7.4, and slightly less preferable are zinc succinate and zinc sulfate which are slightly less ionizable and similar to zinc gluconate in availability of $Zn^{2+}$ ions. Hygroscopic zinc compounds such as zinc chloride are to be wetted and absorbed onto silica gel or other suitable drying absorbent for use in solid compositions. More than one highly ionizable zinc compound other than zinc gluconate in a composition is anticipated. Mixtures of highly ionizable zinc compounds mixed with zinc compounds having first stability constants greater than 2 are anticipated and discouraged for use in treating common colds as efficacy is diminished with reduced availability of $Zn^{2+}$ ions unless extra zinc is added to compensate.

$Zn^{2+}$ releasing solid oral compositions can be prepared by direct compression of ingredients into lozenges, troches, tablets and similar solid forms. ZIA values assume 9 treatments per day.

To make a 5-gram fructose and dextrose based directly compressed tablet containing 23 mg zinc, mix a sufficient amount of a highly ionizable zinc compound excluding zinc gluconate to provide 23 mg zinc, 1 to 17 mg peppermint oil plated onto 4 to 60 mg silica gel, respectively, 25 to 75 mg magnesium stearate (lubricant), about 2400 mg Mendell Emdex ® and sufficient crystalline fructose to make a five gram lozenge. Compress with tablet press using sufficient pressure to obtain maximum dissolution rate. About 8 to 12 tons of pressure on a properly prepared ⅞ inch diameter 5-gram lozenge results in a 15 to 20 minute dissolution rate in water bath testers and 30 minute dissolution times in the oral cavity of a human. Such compositions are non-toxic, thermally, chemically and flavor stable having a pleasant taste and aftertaste which is suitable to treat common colds, reduce common colds or cure common colds in humans in need of such treatment. If compressed to maximum hardness and oral dissolution occurs in about 30 minutes, ZIA value is about 160.

To make a 5-gram sucrose based directly compressible tablet containing 23 mg zinc, mix sufficient highly ionizable zinc compound excluding zinc gluconate to provide 23 mg zinc, saccharin (1 to 50 mg as desired), 1 to 17 mg peppermint oil plated onto silica gel, 25 to 75 mg magnesium stearate and sufficient sucrose (Mendell Sugartab ®) to make a five gram lozenge. Compress into tablet. Such composition is non-toxic, thermally, chemically and flavor stable having a pleasant taste and aftertaste which may be used to treat common colds, reduce the duration of common colds or cure common colds in humans in need of such treatment. If compressed to maximum hardness and oral dissolution occurs in about 18 minutes, ZIA value is about 120.

To make a 3.5-gram dextrose based directly compressible tablet containing 23 mg zinc, mix sufficient highly ionizable zinc compound excluding zinc gluconate to provide 15 mg zinc, saccharin (1 to 10 mg as desired), 1 to 17 mg peppermint oil plated onto silica gel, 25 to 75 mg magnesium stearate and sufficient dextrose (Mendell Emdex ®) to make a 3.5 gram ¾ inch diameter lozenge. Compress into tablet. Such composition is non-toxic, thermally, chemically and flavor stable having a pleasant taste and aftertaste which may be used to treat common colds, reduce the duration of common colds or cure common colds in humans in need of such treatment. If compressed to maximum hardness and oral dissolution occurs in about 20 minutes, ZIA value is about 150.

To make a 5-gram dextrose, fructose, maltose, and isomaltose based directly compressible tablet containing 23 mg zinc, mix sufficient highly ionizable zinc compound excluding zinc gluconate to provide 23 mg zinc, saccharin (1 to 30 mg if desired), 5 to 17 mg peppermint oil plated onto silica gel, 25 to 75 mg magnesium stearate and sufficient Mendell Sweetrex ® to make a five gram lozenge. Compress into tablet. Such composition is non-toxic, thermally, chemically and flavor stable having a pleasant taste and aftertaste which may be used to treat common colds, reduce the duration of common colds or cure common colds in humans in need of such treatment. If compressed to maximum hardness and oral dissolution occurs in about 36 minutes, ZIA value is about 180.

To make a 5-gram fructose and sucrose based directly compressible tablet containing 23 mg zinc, mix sufficient highly ionizable zinc compound excluding zinc gluconate to provide 23 mg zinc, saccharin (1 to 30 mg if desired), 1 to 15 mg peppermint oil plated onto silica gel, 50 to 75 mg magnesium stearate and 2.0 to 3.5 grams crystalline fructose and sufficient sucrose (Mendell Sugartab ®) to make a five gram lozenge. Compress into tablet. Such composition is non-toxic, thermally, chemically and flavor stable having a pleasant taste and aftertaste which may be used to treat common colds, reduce the duration of common colds or cure common colds in humans in need of such treatment. If compressed to maximum hardness and oral dissolution occurs in about 20 minutes, ZIA value is about 120.

To make a 2.5-gram lactose based lozenge containing 10 mg zinc, mix sufficient highly ionizable zinc compound excluding zinc gluconate to provide 10 mg zinc, saccharin (up to 30 mg if desired), about 200 mg wintergreen oil/beta-cyclodextrin complex or other flavor as desired, 50 to 75 mg magnesium stearate and sufficient directly compressible non-palpable lactose to make a 2.5 gram lozenge. Compress with tablet press using sufficient pressure to obtain desired dissolution rate. Such composition is non-toxic, thermally, chemically and flavor stable having a pleasant taste and aftertaste which may be used to treat common colds, reduce the duration of common colds or cure common colds in humans in need of such treatment. If compressed to maximum hardness and oral dissolution occurs in about 30 minutes, ZIA value is about 70.

To make a 3.8-gram hard candy lozenge containing 23 mg zinc, mix anhydrous highly ionizable zinc compound excluding zinc gluconate sufficient to provide 23 mg zinc, flavorings in silica gel, and mix into a heated, molten hard candy base of sucrose and corn syrup, with or without saccharin as desired. Such composition is non-toxic, thermally, chemically and flavor stable having a pleasant taste and aftertaste which may be used to treat common colds, reduce the duration of common colds or cure common colds in humans in need of such treatment. If oral dissolution occurs in about 10 minutes, ZIA value is about 60.

To make a syrup wherein each 7.5 milliliter dose contains about 23 mg zinc from a highly ionizable zinc compound excluding zinc gluconate and zinc chloride, add to 3 grams of deionized water, 4.5 grams of fructose or sucrose, sufficient highly ionizable zinc compound to provide 23 mg zinc, saccharin as desired, and flavors as desired. Vary amount of water and fructose to make other liquids such as mouth washes, gargles, and sprays. Such composition shall be non-toxic, thermally, chemically and flavor stable and have a pleasant taste which may be used to treat common colds, reduce the duration of common colds or cure common colds in humans in need of such treatment. If oral application occurs in about 15 minutes, ZIA value is about 50.

To make a chewing gum wherein each stick releases 15 mg zinc, add to 4 grams of melted chewing gum base, about 5 grams of fructose, anhydrous highly ionizable zinc compound excluding zinc gluconate sufficient to provide 15 mg zinc, saccharin as desired and flavors as desired. Shape and let cool. To make a soft candy, substitute soft candy for chewing gum base. Such compositions shall be non-toxic, thermally, chemically and flavor stable having a pleasant taste and aftertaste which may be used to treat common colds, reduce the duration of common colds or cure common colds in humans in need of such treatment. If oral dissolution occurs in about 10 minutes, ZIA value is about 40.

COMMENTS AND OTHER EXAMPLES

Preferred Zinc Composition

The zinc compound for use in solid non-toxic, flavor-stable zinc compositions having no unpleasant aftertaste for oral absorption is selected from the group of highly ionizable zinc compounds excluding zinc gluconate having a first stability constant less than about log $K_1=2$ and preferably less than log $K_1=1.0$. The preferred method of applying highly ionizable zinc compounds to the oral mucosa is with compressed tablets, lozenges, having a directly compressible dextrose base as they require less dextrose to dissolve in 30 minutes than any other sweet tablet base which allows lozenges to be prepared in the 3 to 3.8 gram size. Lozenges larger than about 5 grams are not well received by subjects as they are perceived as being "too large". The preferred method to prepare flavor oils is by plating them onto silica gel, as potential for chelating zinc by flavor stabilizers is essentially eliminated. Other methods of drying flavor oils are well known in the art and are anticipated. All ingredients to be used in compositions within the present invention are consumable (meaning non-toxic, dissolvable, swallowable, suckable, chewable and so forth), and are believed safe for human consumption.

Importance of Invention

Non-toxic, flavor-stable solid oral zinc compositions are important in that a soluble and highly ionizable zinc compound, zinc gluconate, has been demonstrated useful in lozenge form to treat common colds, reduce the duration of common colds or cure common colds in humans in need of such treatment. Highly ionizable zinc compounds are often more soluble and more ionizable than zinc gluconate, offering improved performance in treating common colds, reducing the duration of common colds or curing common colds in humans in need of such treatment. Highly ionizable zinc compounds are known to be as antirhinoviral and as protective of cells in vitro as interferon. Common colds often require ZIA 100 oral zinc treatment about every two wakeful hours in order to reduce their duration by about 7 days. Non-toxic, highly palatable oral zinc compositions are needed as encouragement for a person in need of such treatment to continue treatment until symptoms are eliminated. The above examples serve to demonstrate that palatable highly ionizable zinc compound lozenges and other oral compositions without unpleasant aftertaste are possible using a fructose, sucrose or other sweet diluent with neither amino acids nor anethole. The examples also show that compositions can retain their pleasant flavor for commercially interesting periods of time.

Release Rates

As will be apparent from examples, the amount of $Zn^{2+}$ ion which will be released can be controlled by the amount of highly ionizable zinc compound incorporated in compositions. As will be readily understood, if compositions with a larger or smaller ratio of fructose or sucrose or other sweet base to zinc is used, that such is anticipated. Also, as will be readily understood, other release rates of $Zn^{2+}$ and fructose, sucrose or other bases are possible and anticipated and may have different ZIA and accordingly produce different treatment responses. Any appropriate means of extended or sustained oral contact administration such as different size lozenges, hard molded candies, syrups, mouth washes, gargles, tooth pastes, tablets, liquids, chewing gums, powders, sprays, aerosols and various similar means and combinations may be used and are anticipated. Any means suitable for delivery of highly soluble and highly ionizable zinc compounds and a consumable, pharmaceutically acceptable carrier to oral and oropharyngeal mucous membranes to permit a pleasant, prolonged, sustained contact of zinc in the mouth, including electrical activation or stimulation, may be used and is anticipated. The present invention provides pleasant, new means of releasing zinc in the oral cavity, in various amounts, and at various rates determined by the formulation and composition used in a manner that is a substantial improvement in flavor, thermal and chemical stability over plain zinc compounds, especially zinc gluconate. As will be apparent to one skilled in the art, variations can be made within the scope of the aforesaid description. Such variations being within the ability of one skilled in the art form a part of the present invention and are embraced by following claims.

I claim:

1. A flavor-stable, pleasant tasting composition for sustained release of $Zn^{2+}$ ions within the oral cavity of a human comprising a highly ionizable zinc compound in combination with a pharmaceutically acceptable carrier wherein said composition excludes flavor masking amounts of anethole and flavor masking amounts of strong zinc chelators.

2. The composition of claim 1 wherein said highly ionizable zinc compound is zinc acetate.

3. The composition of claim 1 wherein said highly ionizable zinc compound is selected from the group consisting of zinc propionate, zinc butyrate, zinc beta-hydroxybutyrate, zinc benzoate, zinc formate, and mixtures thereof.

4. The composition of claim 1 wherein said composition is sweet.

5. The composition of claim 1 wherein said composition is a solid.

6. The composition of claim 5 wherein said composition is a powder.

7. The composition of claim 5 wherein said composition is a compressed tablet.

8. The composition of claim 1 wherein said composition is a liquid.

9. The liquid of claim 8 wherein said liquid excludes zinc chloride.

10. The composition of claim 1 wherein said composition is soft.

11. The composition of claim 1 wherein said composition is free of therapeutically effective amounts of added dental desensitizers and other medicinal agents for oral and dental hygiene.

12. A pleasant tasting, flavor-stable composition for sustained release of $Zn^{2+}$ ions for curing common colds, reducing the duration of common colds, treating common colds, treating common cold symptoms, and treating upper respiratory allergies for use within the oral cavity of a human in need of treatment comprising a therapeutically effective amount of a highly ionizable zinc compound in combination with a sweet pharmaceutically acceptable carrier wherein said composition excludes flavor masking amounts of anethole and flavor masking amounts of strong zinc chelators.

13. The composition of claim 12 wherein said highly ionizable zinc compound is zinc acetate.

14. A pleasant tasting, flavor-stable, solid composition for sustained release of $Zn^{2+}$ ions within the oral cavity of a human consisting essentially of a therapeutically effective amount of one or more highly ionizable zinc compounds in combination with one or more sweet pharmaceutically acceptable carriers and one or more pharmaceutical necessities wherein said composition excludes flavor masking amounts of anethole and flavor masking amounts of strong zinc chelators.

15. The composition of claim 14 wherein said highly ionizable zinc compound is zinc acetate.

16. A method of curing common colds in a human in need of treatment comprising application of the composition of claim 14 to the oral and oropharyngeal membranes of a human sufficiently often to be therapeutically effective.

17. A method of reducing the duration of common cold in a human in need of treatment comprising application of the composition of claim 14 to the oral and oropharyngeal membranes of a human sufficiently often to be therapeutically effective.

18. A method of treating common colds in a human in need of treatment comprising application of the composition of claim 14 to the oral and oropharyngeal membranes of a human sufficiently often to be therapeutically effective.

19. A method of treating common cold symptoms in a human in need of treatment comprising application of the composition of claim 14 to the oral and oropharyngeal membranes of a human sufficiently often to be therapeutically effective.

20. A method of treating upper respiratory allergy in a human in need of treatment comprising application of the composition of claim 14 to the oral and oropharyngeal membranes of a human sufficiently often to be therapeutically effective.

21. A method of providing nutritional supplementation in a human in need of treatment comprising application of the composition of claim 14 to the oral and oropharyngeal membranes of a human sufficiently often to be therapeutically effective.

22. A pleasant tasting, flavor-stable, solid composition for sustained release of $Zn^{2+}$ ions within the oral cavity of a human comprising therapeutically effective amounts of zinc gluconate in combination with a pharmaceutically acceptable carrier consisting essentially of fructose and one or more pharmaceutical necessities other than tablet binding amounts of hydroxypropyl methylcellulose wherein said composition excludes flavor masking amounts of anethole and flavor masking amounts of strong zinc chelators, and said composition is free of therapeutically effective amounts of added dental desensitizers and other medicinal agents for oral and dental hygiene.

23. A method of treating common colds, shortening the duration of common colds, curing common colds, treating upper respiratory allergy, and providing nutritional supplementation in a human in need of treatment comprising application of the composition of claim 22 to the oral and oropharyngeal membranes of a human sufficiently often to be therapeutically effective.

* * * * *

UNITED STATES PATENT AND TRADEMARK OFFICE
CERTIFICATE OF CORRECTION

PATENT NO. : 5,409,905
DATED : April 25, 1995
INVENTOR(S) : George A. Eby, III

It is certified that error appears in the above-indentified patent and that said Letters Patent is hereby corrected as shown below:

On the title page, item [54], and column 1, line 2, change "COMMOND" to --COMMON--.

Signed and Sealed this

Twenty-eighth Day of May, 1996

Attest:

BRUCE LEHMAN

*Attesting Officer*   *Commissioner of Patents and Trademarks*

(12) EX PARTE REEXAMINATION CERTIFICATE (5222nd)
United States Patent
Eby, III

(10) Number: US 5,409,905 C1
(45) Certificate Issued: *Oct. 25, 2005

(54) COMMON COLD TREATMENTS

(75) Inventor: George A. Eby, III, 2109 Paramount Ave., Austin, TX (US) 78704

(73) Assignee: George A. Eby, III, Austin, TX (US)

Reexamination Request:
No. 90/004,518, Feb. 10, 1997

Reexamination Certificate for:
Patent No.: 5,409,905
Issued: Apr. 25, 1995
Appl. No.: 08/215,008
Filed: Mar. 21, 1994

(*) Notice: This patent is subject to a terminal disclaimer.

Certificate of Correction issued May 28, 1996.

Related U.S. Application Data

(63) Continuation of application No. 08/042,473, filed on Apr. 2, 1993, now abandoned, which is a continuation-in-part of application No. 07/799,607, filed on Nov. 27, 1991, now Pat. No. 5,286,748, which is a continuation-in-part of application No. 07/633,043, filed on Dec. 24, 1990, now Pat. No. 5,095,035, which is a continuation-in-part of application No. 07/182,983, filed on Apr. 18, 1988, now Pat. No. 5,002,970, and a continuation-in-part of application No. 07/102,750, filed on Sep. 24, 1987, now Pat. No. 4,956,385, which is a continuation of application No. 06/667,097, filed on Nov. 1, 1984, now abandoned, which is a continuation-in-part of application No. 06/378,479, filed on May 14, 1982, now Pat. No. 4,503,070, which is a continuation-in-part of application No. 06/288,750, filed on Jul. 31, 1981, now abandoned, which is a continuation-in-part of application No. 06/222,620, filed on Jan. 5, 1981, now abandoned.

(51) Int. Cl.$^7$ .............................. A61K 9/14; A61K 9/20; A61K 31/315; A61K 33/30

(52) U.S. Cl. .................... 514/23; 514/494; 514/777; 514/849; 514/888; 514/948; 514/964; 514/965; 514/974; 424/641; 424/643; 424/435; 424/440; 424/451; 424/457; 424/464; 424/468; 424/489

(58) Field of Search ............................ 514/23, 494, 777, 514/849, 888, 948, 964, 965, 974, 889; 424/641, 643, 435, 440, 451, 457, 464, 468, 489

(56) References Cited

U.S. PATENT DOCUMENTS

| | | | | |
|---|---|---|---|---|
| 4,022,880 A | * | 5/1977 | Vinson et al. ................. | 424/49 |
| 4,160,821 A | * | 7/1979 | Sipos .......................... | 424/49 |
| 4,226,851 A | * | 10/1980 | Sompayrac ................... | 424/53 |
| 4,229,430 A | * | 10/1980 | Fahim et al. ................. | 424/49 |
| 4,376,115 A | * | 3/1983 | McCrorey .................... | 424/145 |
| 4,568,540 A | * | 2/1986 | Asano et al. .................. | 424/52 |
| 4,664,906 A | * | 5/1987 | Sipos ........................... | 424/49 |
| 4,871,532 A | * | 10/1989 | Hoogendoorn ............... | 424/50 |
| 5,059,416 A | * | 10/1991 | Cherukuri et al. ............ | 424/48 |

FOREIGN PATENT DOCUMENTS

| | | | |
|---|---|---|---|
| EP | 0181161 | * | 5/1986 |
| EP | 0381522 | * | 8/1990 |

OTHER PUBLICATIONS

The Condensed Chemical Dictionary, Tenth Edition, Hawley, p. 408, 1981.*
Webster's New Universal Unabridged Dictionary, Barnes and Noble Books, p. 386, 1992.*
Eby, George A, "Handbook for Curing the Common Cold (or Making it Worse)," George A Eby (ed.), Morgan Printing, Austin, Texas, Apr. 20, 1992.
Eby, George A, "Handbook for Curing the Common Cold—The Zinc Lozenge Story," George A Eby (ed.), Morgan Printing, Austin, Texas, Feb. 14, 1994.

* cited by examiner

*Primary Examiner*—John Pak

(57) ABSTRACT

Present invention is a non-toxic, flavor stable, pleasant tasting composition releasing $Zn^{2+}$ from compositions containing a highly ionizable zinc compound other than zinc gluconate that reduces the duration of common colds in humans. The composition is used in the oral cavity of a human suffering from a common cold. The composition comprises highly ionizable zinc compounds and a pharmaceutically acceptable carrier such as fructose, dextrose or sucrose with various additions. Compositions are unique in that they are non-toxic, pleasant tasting and do not have an offensive aftertaste, yet deliver zinc ions into oral tissues which may be used to treat common colds, reduce the duration of common colds or cure common colds in humans in need of such treatment. Compositions are non-toxic, thermally, chemically and flavor stable. The compositions may be prepared in the form of compressed tablets, lozenges, powders, liquids or chewing gums. Present compositions deliver strongly antirhinoviral and interferon inducing $Zn^{2+}$ ions to the oral mucosa of a human. In vitro, $Zn^{2+}$ is an antirhinoviral and as protective of cell monolayers as interferon and is also a potent interferon inducer. Said pleasant tasting composition is an improvement upon a slow-release candy composition comprising a hard candy base, highly ionizable zinc compounds and an amino acid; and said composition is an improvement upon a medicinal composition for release of zinc ion consisting essentially of a suitable pharmaceutical carrier, highly ionizable zinc compounds and anethole.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 4–23:

This application is a continuation of application Ser. No. 08/042,473, filed on Apr. 2, 1993, now abandoned, which is a continuation-in-part of U.S. Ser. No. 07/799,607, filed Nov. 27, 1991, [abandoned] *now U.S. Pat. No. 5,286,748*, which is a continuation-in-part of U.S. Ser. No. 07/633,043, filed Dec. 24, 1990, now U.S. Pat. No. 5,095,035, which is a continuation-in-part application of U.S. Ser. No. 07/182,983, filed Apr. 18, 1988, now U.S. Pat. No. 5,002,970, and a continuation-in-part of application U.S. Ser. No. 07/102,750, filed Sep. 24, 1987, now U.S. Pat. No. 4,956,385, which is continuation of application Ser. No. 06/667,097, filed Nov. 1, 1984, now abandoned, which is a continuation-in-part application of Ser. No. 06/378,479, filed May 14, 1982, now U.S. Pat. No. 4,503,070, issued Mar. 5, 1985, reissued on Nov. 27, 1990, as RE 33,465, which is a continuation-in-part application of U.S. Ser. No. 06/288,750, filed Jul. 31, 1981, now abandoned, which is a continuation-in-part application of U.S. Ser. No. 06/222,620, filed Jan. 5, 1981, now abandoned.

AS A RESULT OF REEXAMINATION, IT HAS BEEN DETERMINED THAT:

Claims 8–9, 14–16 and 21–22 are cancelled.

Claims 1–7, 10–13, 17–20 and 23 are determined to be patentable as amended.

New claims 24–36 are added and determined to be patentable.

1. A *method of treating the common cold in a human in need of treatment comprising application of a* flavor-stable, pleasant tasting composition *in a solid, chewable or paste form* for sustained release of $Zn^{2+}$ ions within the oral cavity of a human comprising a highly ionizable zinc compound in combination with a pharmaceutically acceptable carrier wherein said composition excludes flavor masking amounts of anethole and flavor masking amounts of strong zinc chelators *and wherein said highly ionizable zinc compound is not zinc chloride or zinc gluconate, to the oral or oropharyngeal mucosa of the human in a manner to be therapeutically effective.*

2. The [composition] *method* of claim 1 wherein said highly ionizable zinc compound is zinc acetate.

3. The [composition] *method* of claim 1 wherein said highly ionizable zinc compound is selected from the group consisting of zinc propionate, zinc butyrate, zinc betahydroxybutyrate, zinc benzoate, zinc formate, and mixtures thereof.

4. The [composition] *method* of claim 1 wherein said composition is sweet.

5. The [composition] *method* of claim 1 wherein said composition is a solid.

6. The [composition] *method* of claim 5 wherein said composition is a powder.

7. The [composition] *method* of claim 5 wherein said composition is a compressed tablet.

10. The [composition] *method* of claim 1 wherein said composition is soft.

11. The [composition] *method* of claim 1 wherein said composition is free of therapeutically effective amounts of added dental desensitizers and other medicinal agents for oral and dental hygiene.

12. A *method of treating the common cold in a human in need of treatment comprising application of a* pleasant tasting, flavor-stable composition *in solid, chewable or paste form* for sustained release of $Zn^{2+}$ ions for [curing common colds,] reducing the duration of common colds, treating common colds, treating common cold symptoms, and treating upper respiratory allergies for use within the oral cavity of a human in need of treatment comprising a therapeutically effective amount of a highly ionizable zinc compound in combination with a sweet pharmaceutically acceptable carrier wherein said composition excludes flavor masking amounts of anethole and flavor masking amounts of strong zinc chelators *and wherein said highly ionizable zinc compound is not zinc chloride or zinc gluconate, to the oral or oropharyngeal mucosa of the human in a manner to be therapeutically effective.*

13. The [composition] *method* of claim 12 wherein said highly ionizable zinc compound is zinc acetate.

17. A method of reducing the duration of common cold in a human in need of treatment comprising application of [the composition of claim 14] *a pleasant tasting, flavor-stable, solid composition for sustained release of $Zn^{2+}$ ions within the oral cavity of a human consisting essentially of a therapeutically effective amount of one or more highly ionizable zinc compounds in combination with one or more sweet pharmaceutically acceptable carriers and one or more pharmaceutical necessities wherein said composition excludes flavor masking amounts of anethole and flavor masking amounts of strong zinc chelators and wherein said highly ionizable zinc compound is not zinc gluconate,* to the oral and oropharyngeal membranes of a human sufficiently often to be therapeutically effective.

18. A method of treating common colds in a human in need of treatment comprising application of [the composition of claim 14] *a pleasant tasting, flavor-stable, solid composition for sustained release of $Zn^{2+}$ ions within the oral cavity of a human consisting essentially of a therapeutically effective amount of one or more highly ionizable zinc compounds in combination with one or more sweet pharmaceutically acceptable carriers and one or more pharmaceutical necessities wherein said composition excludes flavor masking amounts of anethole and flavor masking amounts of strong zinc chelators and wherein said highly ionizable zinc compounds is not zinc gluconate,* to the oral 19. A method of treating common cold symptoms in a human in need of treatment comprising application of [the composition of claim 14] *a pleasant tasting, flavor-stable, solid composition for sustained release of $Zn^{2+}$ ions within the oral cavity of a human consisting essentially of a therapeutically effective amount of one or more highly ionizable zinc compounds in combination with one or more sweet pharmaceutically acceptable carriers and one or more pharmaceutical necessities wherein said composition excludes flavor masking amounts of anethole and flavor masking amounts of strong zinc chelators and wherein said highly ionizable zinc compound is not zinc gluconate* to the oral and oropharyngeal membranes of a human sufficiently often to be therapeutically effective.

20. A method of treating upper respiratory allergy in a human in need of treatment comprising application of [the composition of claim 14] *a pleasant tasting, flavor-stable, solid composition for sustained release of $Zn^{2+}$ ions within the oral cavity of a human consisting essentially of a therapeutically effective amount of one or more highly ionizable zinc compounds in combination with one or more sweet pharmaceutically acceptable carriers and one or more pharmaceutical necessities wherein said composition excludes flavor masking amounts of anethole and flavor masking amounts of strong zinc chelators and wherein said highly ionizable zinc compound is not zinc gluconate,* to the oral and oropharyngeal membranes of a human sufficiently often to be therapeutically effective.

23. A method of treating common colds, shortening the duration of common colds, [curing common colds,] treating upper respiratory allergy, and providing nutritional supplementation in a human in need of treatment comprising application of [the composition of claim 22] *a pleasant tasting, flavor-stable, solid composition for sustained release of $Zn^{2+}$ ions within the oral cavity of a human comprising therapeutically effective amounts of zinc gluconate in combination with a pharmaceutically acceptable carrier consisting essentially of fructose and one or more pharmaceutical necessities other than tablet binding amounts of hydroxypropyl methylcellulose wherein said composition excludes flavor masking amounts of anethole and flavor masking amounts of strong zinc chelators, and said composition is free of therapeutically effective amounts of added dental desensitizers and other medicinal agents for oral and dental hygiene* to the oral and oropharyngeal membranes of a human sufficiently often to be therapeutically effective.

*24. The method of claim 1, wherein the composition is in a solid form comprising a lozenge designed for repetitive consumption in a manner effective for treating a common cold or its symptoms.*

*25. The method of claim 24, further comprising a pharmaceutical necessity.*

*26. The method of claim 25, wherein the pharmaceutically necessity comprises a sweetener.*

*27. The method of claim 26, wherein at least one sweetener is selected from the group consisting of corn syrup, fructose, sucrose, lactose, and dextrose.*

*28. The method of claim 27, wherein the sweetener is a mixture of corn syrup and sucrose.*

*29. The method of claim 25, wherein the pharmaceutical necessity comprises silica gel.*

*30. The method of claim 25, wherein the pharmaceutical necessity comprises a flavoring.*

*31. The method of claim 30, wherein the flavoring is selected from the group consisting of cherry, cinnamon, peppermint, methyl salicylate, menthol, and eucalyptol.*

*32. The method of claim 31, wherein the flavoring is peppermint.*

*33. The method of claim 25, wherein the pharmaceutical necessity comprises a tablet lubricant.*

*34. The method of claim 33, wherein the tablet lubricant comprises magnesium stearate.*

*35. The method of claim 24, wherein the lozenge further comprises saccharin.*

*36. The method of claim 35, wherein the lozenge comprises between about 1 and about 50 mg of saccharin.*

* * * * *